United States Patent
Schaff et al.

(10) Patent No.: US 9,186,668 B1
(45) Date of Patent: Nov. 17, 2015

(54) MICROFLUIDIC DEVICES, SYSTEMS, AND METHODS FOR QUANTIFYING PARTICLES USING CENTRIFUGAL FORCE

(75) Inventors: Ulrich Y. Schaff, Davis, CA (US); Gregory J. Sommer, Livermore, CA (US); Anup K. Singh, Danville, CA (US)

(73) Assignee: Sandia Corporation, Albuquerque, NM (US)

( * ) Notice: Subject to any disclaimer, the term of this patent is extended or adjusted under 35 U.S.C. 154(b) by 409 days.

(21) Appl. No.: 12/891,956

(22) Filed: Sep. 28, 2010

Related U.S. Application Data

(60) Provisional application No. 61/351,458, filed on Jun. 4, 2010.

(51) Int. Cl.
| | |
|---|---|
| *C12Q 1/68* | (2006.01) |
| *C12M 1/34* | (2006.01) |
| *G01N 33/53* | (2006.01) |
| *B01L 3/02* | (2006.01) |
| *B01L 3/00* | (2006.01) |

(52) U.S. Cl.
CPC ............... *B01L 3/502* (2013.01); *B01L 3/0275* (2013.01)

(58) Field of Classification Search
CPC .......... B01L 2400/0409; B01L 3/5027; C12Q 1/6883
See application file for complete search history.

(56) References Cited

U.S. PATENT DOCUMENTS

| | | | |
|---|---|---|---|
| 3,555,284 A | 1/1971 | Anderson | |
| 3,744,974 A | 7/1973 | Maddox | |
| 4,125,375 A | 11/1978 | Hunter | |
| 4,156,570 A | 5/1979 | Wardlaw | 356/36 |
| 4,656,143 A | 4/1987 | Baker et al. | |
| 4,683,579 A | 7/1987 | Wardlaw | 377/11 |
| 4,844,818 A | 7/1989 | Smith | |
| 5,279,936 A | 1/1994 | Vorpahl | |
| 5,635,362 A | 6/1997 | Levine et al. | |
| 5,705,628 A | 1/1998 | Hawkins | |

(Continued)

FOREIGN PATENT DOCUMENTS

| | | |
|---|---|---|
| WO | WO-2008/143578 | 11/2008 |
| WO | WO 2008/143578 | * 11/2008 |
| WO | WO-2009/098237 | 8/2009 |

OTHER PUBLICATIONS

Amersham, "Percoll: Methodology and Applications", 2001, pp. 1-84.*

(Continued)

*Primary Examiner* — Betty Forman
(74) *Attorney, Agent, or Firm* — Dorsey & Whitney, LLP

(57) ABSTRACT

Embodiments of the present invention are directed toward microfluidic systems, apparatus, and methods for measuring a quantity of cells in a fluid. Examples include a differential white blood cell measurement using a centrifugal microfluidic system. A method may include introducing a fluid sample containing a quantity of cells into a microfluidic channel defined in part by a substrate. The quantity of cells may be transported toward a detection region defined in part by the substrate, wherein the detection region contains a density media, and wherein the density media has a density lower than a density of the cells and higher than a density of the fluid sample. The substrate may be spun such that at least a portion of the quantity of cells are transported through the density media. Signals may be detected from label moieties affixed to the cells.

19 Claims, 10 Drawing Sheets

(56) References Cited

U.S. PATENT DOCUMENTS

| | | | |
|---|---|---|---|
| 5,882,903 | A | 3/1999 | Andrevski et al. |
| 6,153,148 | A | 11/2000 | Thomas .......................... 422/72 |
| 6,319,469 | B1 | 11/2001 | Mian et al. ...................... 422/64 |
| 6,503,722 | B1 | 1/2003 | Valkirs |
| 6,887,384 | B1 | 5/2005 | Frechet et al. |
| 6,960,449 | B2 | 11/2005 | Wang et al. |
| 7,033,747 | B2 | 4/2006 | Gordon |
| 7,157,049 | B2 | 1/2007 | Valencia et al. ............. 422/68.1 |
| 7,312,085 | B2 | 12/2007 | Chou et al. |
| 7,758,810 | B2 | 7/2010 | Lee et al. ........................ 422/72 |
| 2001/0055812 | A1 | 12/2001 | Mian et al. |
| 2002/0098535 | A1* | 7/2002 | Wang et al. .................. 435/40.5 |
| 2002/0137068 | A1 | 9/2002 | Haugland et al. |
| 2002/0151043 | A1 | 10/2002 | Gordon |
| 2002/0164659 | A1 | 11/2002 | Rao et al. |
| 2003/0124719 | A1* | 7/2003 | Woodside ...................... 435/325 |
| 2004/0072278 | A1* | 4/2004 | Chou et al. ....................... 435/29 |
| 2005/0215410 | A1 | 9/2005 | Merino et al. |
| 2005/0282220 | A1 | 12/2005 | Prober et al. |
| 2009/0004059 | A1 | 1/2009 | Pugia et al. |
| 2009/0069554 | A1 | 3/2009 | Finne |
| 2009/0209402 | A1* | 8/2009 | Andersson ........................ 494/6 |
| 2009/0325186 | A1 | 12/2009 | Hinnah et al. |
| 2010/0068754 | A1* | 3/2010 | Kirakossian .................... 435/34 |
| 2010/0120596 | A1* | 5/2010 | Froman et al. .................... 494/8 |
| 2010/0151560 | A1 | 6/2010 | Wo et al. |

OTHER PUBLICATIONS

Todd H. Rider et al. "*A B Cell-Based Sensor For Rapid Identification of Pathogens*"; www.sciencemag.org; Science vol. 301; pp. 213-215 (2003).

Madou, M., et al. "*Lab on a CD*"; Annu Rev Biomed Eng 8, 601-628 (2006).

Lim, C.T. & Zhang, Y. "*Bead-Based Microfluidic Immunoassays: The Next Generation*"; Biosens Bioelectron 22, 1197-1204 (2007).

Melissa L. Maes et al. "Comparison of Sample Fixation and the Use of LDS-751 or Anti-CD45 for Leukocyte Identification in Mouse Whole Blood for Flow Cytometry"; Journal of Immunological Methods; pp. 1-13 (2007).

Holmes, D et al; "Leukocyte Analysis and Differentiation Using High Speed Microfluidic Single Cell Impedance Cytometry"; Lab Chip 9, pp. 2881-2889 (2009).

Lee, B.S. et al. "*A Fully Automated Immunoassay From Whole Blood on a Disc*"; Lab Chip 9, pp. 1548-1555 (2009).

Golorikian, H., Zalesk, T. & Clancy, B. "*Overview of Microfluidic Applications in IVDS*". DX Direction 1, pp. 12-16 (2010).

Abi-Samra, Kameel, et al., "Infrared Controlled Waxes for Liquid Handling and Storage on a CD-Microfluidic Platform," The Royal Society of Chemistry, Lab Chip, 2011, pp. 723-726.

Baldwin, Robert L., "How Hofmeister Ion Interactions Affect Protein Stability," Biophysical Journal, vol. 71, Oct. 1996, pp. 2056-2063.

Boyko, Matthew, et al., "Cell-Free DNA—A Marker to Predict Ischemic Brain Damage in a Rat Stroke Experimental Model," J Neurosurg Anesthesiol; vol. 23, No. 3, Jul. 2011, pp. 222-228.

Carney, J., "Rapid Diagnostic Tests Employing Latex Particles," Analytical Proceedings, Apr. 1990, pp. 27:99-100.

Curtis, R.A., et al., "A Molecular Approach to Bioseparations: Protein-Protein and Protein-Salt Interactions," Chemical Engineering Science, 2006, vol. 61, pp. 907-923.

Czeiger, David, et al., "Measurement of Circulating Cell-Free DNA Levels by a New Simple Fluorescent Test in Patients with Primary Colorectal Cancer," Am J Clin Pathol, 2011, vol. 135, pp. 264-270.

Glorikian, Harry, et al., "Smart-Consumables Product Development: Implications for Molecular Diagnostics," DX Directions, Spring 2010, pp. 12-16.

Goldshtein, Hagit, et al., "A Rapid Direct Fluorescent Assay for Cell-Free DNA Quantification in Biological Fluids," Annals of Clinical Biochemistry, 2009, vol. 46, pp. 488-494.

Lo, Y.M.D., et al., "Plasma DNA as a Prognostic Marker in Trauma Patients," Clinical Chemistry 46:3, pp. 319-323, 2000.

Min, Junhong, et al., "Functional Integration of DNA Purification and Concentration into a Real Time Micro-PCR Chip," The Royal Society of Chemistry; Lab Chip, 2011, pp. 259-265.

Price, Christopher P., et al., "Light-Scattering Immunoassay," Principles and Practice Immunoassay (Second Edition), 1997, Chap. 18, pp. 445-480.

Rhodes, Andrew, et al., "Plasma DNA Concentration as a Predictor of Mortality and Sepsis in Critically Ill Patients," Critical Care, 2006, pp. 1-7.

Riegger, L., et al., "Read-Out Concepts for Multiplexed Bead-Based Fluorescence Immunoassays on Centrifugal Microfluidic Platforms," Sensors and Actuators A 126, 2006, 455-462.

Schaff, Ulrich Y., et al., "Whole Blood Immunoassay Based on Centrifugal Bead Sedimentation," Clinical Chemistry, 2011, vol. 57:5, pp. 753-761.

Zhang, L., et al., "A New Biodosimetric Method: Branched DNA-Based Quantitative Detection of B1 DNA in Mouse Plasma," The British Journal of Radiology, 83, Aug. 2010, pp. 694-701.

Ziegler, Annemarie, et al., "Circulating DNA: A New Diagnostic Gold Mine?" Cancer Treatment Reviews, 2002, vol. 28, pp. 255-271.

Ahanotu, et al., "Staphylococcal Enterotoxin B as a Biological Weapon: Recognition, Management, and Surveillance of Staphylococcal Enterotoxin", Applied Biosafety; vol. 11 (3), 2006, 120-126.

Albrecht, J.W. et al., "Micro Free-Flow IEF Enhanced Active Cooling and Functionalized Gels", Electrophoresis, 2006, pp. 4960-4969, vol. 27.

Amersham, "Percoll: Methodology And Applications", 2001, 1-84.

Amukele, et al., "Ricin A-chain activity on stem-loop and unstructured DNA substrates.", Biochemistry; vol. 44(11), Mar. 25, 2005, 4416-4425.

Andersson, et al., "Parallel nanoliter microfluidic analysis system", Clinical Chemistry, 2007.

Berry, Scott M., "One-step Purification of Nucleic Acid for Gene Expression Analysis via Immiscible Filtration Assisted by Surface Tension", Lap Chip, May 21, 2011.

Brigotti, et al., "Shiga toxin 1 acting on DNA in vitro is a heat-stable enzyme not requiring proteolytic activation", Biochimie Journal; 86(45), 2004, 305-309.

Endo, et al., "RNA N-Glycosidase Activity of Ricin A-chain. Mechanism of Action of the Toxic Lectin Ricin on Eukaryotic Ribosomes", The Journal of Biological Chemistry, vol. 262, No. 17, Jun. 15, 1987, 8128-8130.

Gorkin, et al., "Centrifugal microfluidics for biomedical applications", www.rsc.org/loc; Lab on a Chip, May 2010, 1758-1773.

Holmberg, et al., "Depurination of A4256 in 28 S rRNA by the Ribosome-inactivating Proteins from Barley and Ricin Results in Different Ribosome Conformations", Journal of Molecular Biology; vol. 259(1), May 31, 1996, 81-94.

Huang, et al., "The Primary Structure of Staphylococcal Enterotoxin B. III. The Cyanogen Bromide Peptides of Reduced and Aminoethylated Enterotoxin B, and the Complete Amino Acid Sequence.", The Journal of Biological Chemistry vol. 245 No. 14, Jul. 25, 1970, 3518-3525.

International Search Report and Written Opinion dated Jun. 28, 2013 for PCT/US2013/032349.

Lee, et al., "Fully integrated lab-on-a-disc for simultaneous analysis of biochemistry and immunoassay from whole blood", Lab Chip, 2011.

Saukkonen, et al., "Cell-Free Plasma DNA as a Predictor of Outcome in Severe Sepsis and Septic Shock", Clinical Chemistry; vol. 54:6, 2008, 1000-1007.

Schembri, et al., "Portable Simultaneous Multiple Analyte Whole-Blood Analyzer for Point-of-Care Testing", Clinical Chemistry 38/9, 1992, 1665-1670.

(56) References Cited

OTHER PUBLICATIONS

Schneider, et al., "Characterization of EBV-Genome Negative "Null" and "T" Cell Lines Derived From Children With Acute Lymphoblastic Leukemia and Leukemic Transformed Non-Hodgkin Lymphoma", International Journal of Cancer; 19(5), May 15, 1977, 621-626.

Yu, et al., "Bioinformatic processing to identify single nucleotide polymorphism that potentially affect Ape1 function.", Mutation Research/Genetic Toxicology and Environmental Mutagenesis; vol. 722(2), Jun. 17, 2011, 140-146.

McBain et al., Polyethyleneimine functionalized iron oxide nanoparticles as agents for DNA delivery and transfection, Journal of Materials Chemistry, 17, pp. 2561-2565, available online Apr. 12, 2007.

Riahi et al. Analytical Chemistry. 2011. 83(16): 6349-6354 and Supporting Information.

Melting Temperature Calculation. Retrieved on asf from the internet: http://www.biophp.org/minitools/melting_temperature/demo.php?primer=CGT+TAC+CCG+CAG&basic-1&NearestNeighbor=1&cp=200&cs=50&cmg=0.

Berlier at al. The Journal of Histochemistry and Cytochemistry. 2003. 51(12): 1699-1712.

* cited by examiner

MICROFLUIDIC DEVICES, SYSTEMS, AND METHODS FOR QUANTIFYING PARTICLES USING CENTRIFUGAL FORCE

CROSS-REFERENCE TO RELATED APPLICATION(S)

This application claims the benefit of the earlier filing date of U.S. Provisional Application 61/351,458, filed Jun. 4, 2010, entitled "Method for Counting White Blood Cells", which provisional application is hereby incorporated by reference, in its entirety, for any purpose.

STATEMENT REGARDING RESEARCH & DEVELOPMENT

Described examples were made with Government support under Government Contract No. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

TECHNICAL FIELD

Embodiments of the invention relate generally to centrifugal microfluidic systems and examples include methods, systems, and apparatus employing centrifugal forces for quantifying particles in fluid.

BACKGROUND

A variety of diagnostic techniques utilize a cell count from a fluid sample, such as a differential white blood cell count. For example, a differential white blood cell count may be utilized in medical diagnostic techniques for detecting sepsis, leukemia, AIDS, radiation exposure, as well as other conditions. Typical methods for measuring white blood cell count include flow cytometry, electrical impedance counting, and visual counting from a fluid sample under a microscope. See, for example, Holmes, D., et. al. "Leukocyte analysis and differentiation using high speed microfluidic single cell impedance cytometry," *Lab Chip* 9, 2881-2889 (2009), which article is hereby incorporated by reference in its entirety for any purpose. These commonly used techniques may require a large fluid sample for analysis, and may occur as a stand-alone diagnostic procedure. Further, the techniques may require operation by a skilled technician.

Microfluidic systems, including "lab on a chip" or "lab on a disk" systems continue to be in development. See, Lee, B. S., et. al., "A fully automated immunoassay from whole blood on a disc," *Lab Chip* 9, 1548-1555 (2009) and Madou, M. et. al., "Lab on a CD," *Annu. Rev. Biomed Engr.* 8, 601-628 (2006), which articles are hereby incorporated by reference in their entirety for any purpose.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known chemical structures, chemical components, molecules, materials, electronic components, circuits, control signals, timing protocols, and software operations have not been shown in detail in order to avoid unnecessarily obscuring the described embodiments of the invention.

Embodiments of the present invention are directed toward microfluidic systems, apparatus, and methods for quantifying, e.g. counting, a quantity of particles in a fluid. Although examples are described with reference to the measurement of white blood cells and differential white blood cell counting, it is to be understood that other types of cells may also be quantified in an analogous manner. Indeed, in other examples, substantially any particles, including beads, having a characteristic volume and shape may be measured using examples described herein.

Figure 1:
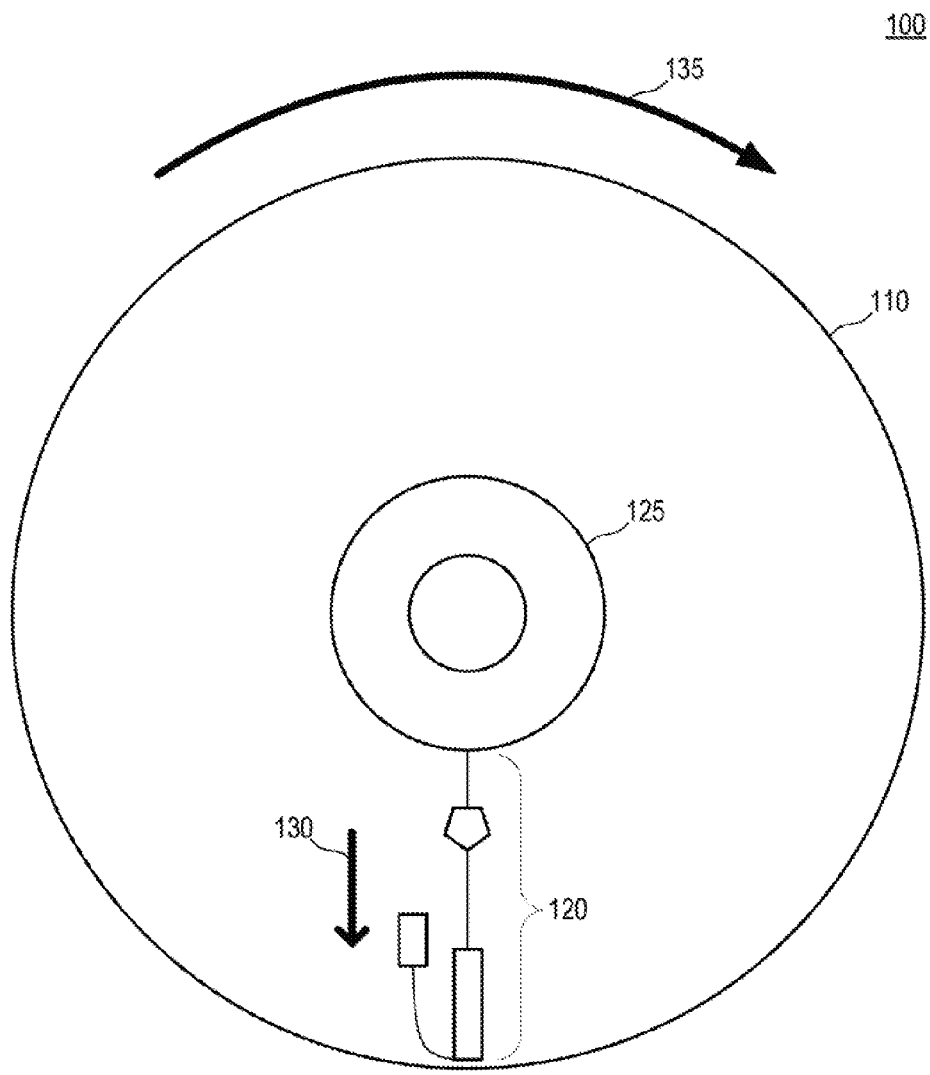
FIG. 1 is a schematic illustration of a microfluidic disk arranged in accordance with embodiments of the present invention.

FIG. 1 is a schematic illustration of a microfluidic disk 100 arranged in accordance with embodiments of the present invention. The microfluidic disk 100 may include a substrate 110 which may at least partially define regions of a cell quantification area 120. The microfluidic disk 100 may include a fluid inlet port 125 in fluid communication with the cell quantification area 120. During operation, as will be described further below, fluid, including a quantity of cells in the fluid, may be transported using centrifugal force from an interior of the microfluidic disk 100 toward a periphery of the microfluidic disk 100 in a direction indicated by an arrow 130. The centrifugal force may be generated by rotating the microfluidic disk 100 in the direction indicated by the arrow 135, or in the opposite direction.

The substrate 110 may be implemented using any of a variety of suitable substrate materials. In some embodiments, the substrate may be a quartz substrate. Quartz, glass, polycarbonate, fused-silica, PDMS, and other transparent substrates may be desired in some embodiments to allow optical observation of sample within the channels and chambers of the disk 100. In some embodiments, however, a plastic, metal or semiconductor substrate may be used. In some embodiments, multiple materials may be used to implement the substrate 110. The substrate 110 may include surface treatments or other coatings, which may in some embodiments enhance compatibility with fluids placed on the substrate 110. In some embodiments surface treatments or other coatings may be provided to control fluid interaction with the substrate 110. While shown as a round disk in FIG. 1, the substrate 110 may take substantially any shape, including square.

The substrate 110 may generally, at least partially, define a variety of microfluidic features. Generally, microfluidic, as used herein, refers to a system, device, or feature having a dimension of around 1 mm or less and suitable for at least partially containing a fluid. In some embodiments, 500 µm or less. In some embodiments, the microfluidic features may have a dimension of around 100 µm or less. Other dimensions may be used. The substrate 110 may define one or more microfluidic features, including any number of channels, chambers, inlet/outlet ports, or other features.

Microscale fabrication techniques, generally known in the art, may be utilized to fabricate the microfluidic disk 100. The microscale fabrication techniques employed to fabricate the disk 100 may include, for example, embossing, etching, injection molding, surface treatments, photolithography, bonding and other techniques.

A fluid inlet port 125 may be provided to receive a fluid that may be analyzed using the microfluidic disk 100. The fluid inlet port 125 may have generally any configuration, and fluid may enter the fluid inlet port 125 utilizing substantially any fluid transport mechanism, including dropping, pipetting, or pumping a fluid sample into the fluid inlet port 125. The fluid inlet port 125 may take substantially any shape. Generally, the fluid inlet port 125 is in fluid communication with the cell quantification area 120. Generally, by fluid communication it is meant that a fluid may flow from one area to the other, either freely or using one or more transport forces and/or valves, and with or without flowing through intervening structures.

The cell quantification area 120 will be described further below, and generally may include one or more microfluidic channels in fluid communication with the fluid inlet port 125. Although a single cell quantification area 120 is shown in FIG. 1, generally any number may be present on the microfluidic disk 100.

As the microfluidic disk 100 is rotated in the direction indicated by the arrow 135 (or in the opposite direction), a centrifugal force may be generated. The centrifugal force may generally transport fluid from the inlet port 125 through the cell quantification area 120.

Figure 2:
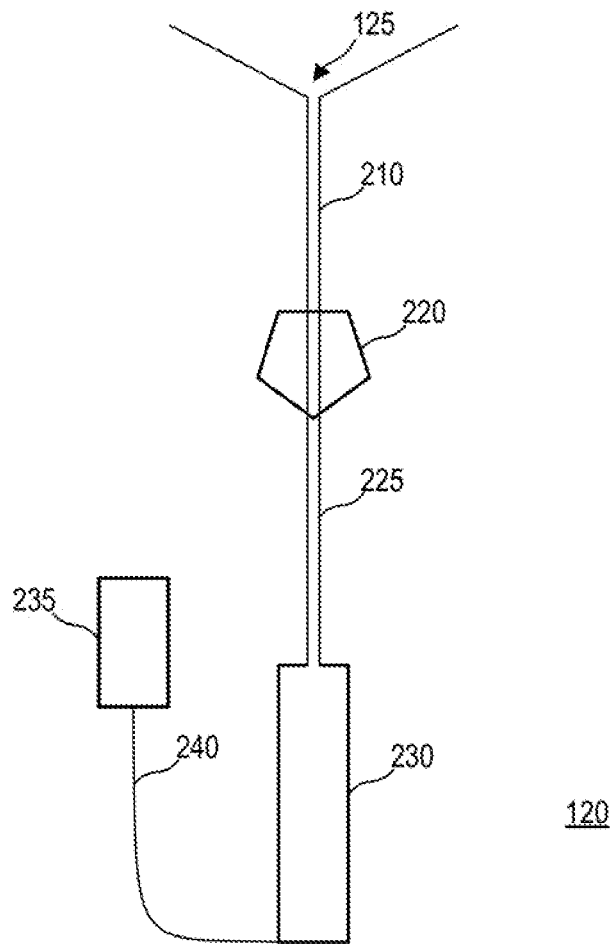
FIG. 2 is a schematic illustration of a cell quantification area of a microfluidic disk in accordance with an embodiment of the present invention.

FIG. 2 is a schematic illustration of a cell quantification area 120 of a microfluidic disk in accordance with an embodiment of the present invention. The cell quantification area 120 includes a microfluidic channel 210 in fluid communication with the fluid inlet port 125. A reservoir 220 is in fluid communication with the microfluidic channel 210. The reservoir 220 is in fluid communication with a detection region 230 via a channel 225. Another reservoir 235 is in fluid communication with the detection region 230 via a channel 240.

The reservoirs 220 and 235 may generally be implemented using any size and shape, and may contain one or more reagents including solids and/or fluids which may interact with fluid entering and/or exiting the reservoir. In some examples, the reservoir 220 is configured to hold lysis agents and/or label moieties. The label moieties may be selected to affix to the cells for quantification. That is, the label moieties may bind or otherwise become affixed to cells and may emit a signal suitable for detection, such as an optical or an electrical signal. For example, to quantify white blood cells, a membrane permeable DNA-specific fluorescent dye may be used, such as lyophilized DNA dye. Many suitable dyes are available, including but not limited to LDS-751. See Maes, M. L., et. al., "Comparison of sample fixation and the use of LDS-751 or anti-CD45 for leukocyte identification in mouse whole blood for flow cytometry," *J. Immunol. Methods* 319, 79-86 (2007), which article is hereby incorporated by reference in its entirety for any purpose. In other examples, labeled antibodies that recognize proteins on the surface of specific cells may be used. Cells labeled in this manner may be separated by size and density as described herein and may be detected using signal detected from the labeled antibodies. For example, a label moiety may include an antibody against CD14 chemically coupled to a fluorescent label moiety. The CD label moiety may then bind to monocytes. Utilizing label moieties specific to one or more particular cell types may aid in the quantification of the labeled cell type relative to others having similar size and/or density, such as but not limited to, T-lymphocytes and/or B-lymphocytes. In some examples, lipid dye molecules may be used as label moieties. Blood cell membranes include lipid bilayers, and lipid dye molecules may accordingly be used as label moieties in some examples. Lipid dye molecules may facilitate detection and/or quantification of red blood cells and platelets in addition to white blood cells in some examples. The lysis agents may include, for example, a detergent such as Saponin for the lysis of red blood cells.

The reservoir 235 may be configured to contain a liquid density media. The density media may have a density lower than a density of the cells to be quantified and higher than a density of the fluid sample. The density media may generally be implemented using a fluid having a density selected to be in the appropriate range—lower than a density of the cells to be quantified and higher than a density of the fluid sample. In some examples, a fluid sample may be diluted for use with a particular density media. The density media may include, for example, a salt solution containing a suspension of silica particles which may be coated with a biocompatible coating. An example of a suitable density media is Percoll™, available from GE Lifesciences. Particular densities may be achieved by adjusting a percentage of Percoll™ in the salt solution. Generally, viscosity and density of the density media may be adjusted by selecting a composition of the media. Varying the concentration of solutes such as sucrose or dextran in the media may adjust the density and/or viscosity.

A table of example densities of particular blood components is provided below in Table 1.

TABLE 1

Example densities of blood components

| Component | Density |
|---|---|
| Whole Blood | 1.06 |
| Plasma | 1.025 |
| Red blood cells | 1.095 |
| Granulocytes | 1.085 |
| Monocytes | 1.07 |
| Lymphocytes | 1.07 |

Accordingly, a suitable density media to quantify white blood cells in accordance with examples of the present invention (including granulocytes, monocytes, and lymphocytes) may have a density between 1.06 and 1.07. In some examples, a whole blood sample may be diluted to a lower density to allow for a larger range of acceptable density media. In one example, a whole blood fluid sample may be diluted using a salt solution, such as PBS, to a density of around 1.03. A suitable density media may then have a density between about 1.03 and 1.07. For example, a density media having a density of 1.06 may be used.

The detection region 230 may be a channel or chamber and may vary in configuration in accordance with the detection technique employed, as will be described further below. The detection region 230 may generally be configured to allow for detection of a signal emitted by label moieties affixed to the cells to be quantified.

As will be described further below, centrifugal forces may generally be used to transport a fluid sample including cells to be quantified from the inlet port 125 toward the detection region 230. Additionally, centrifugal forces may be used to transport density media from the reservoir 235 to the detection region 230.

Figure 3:
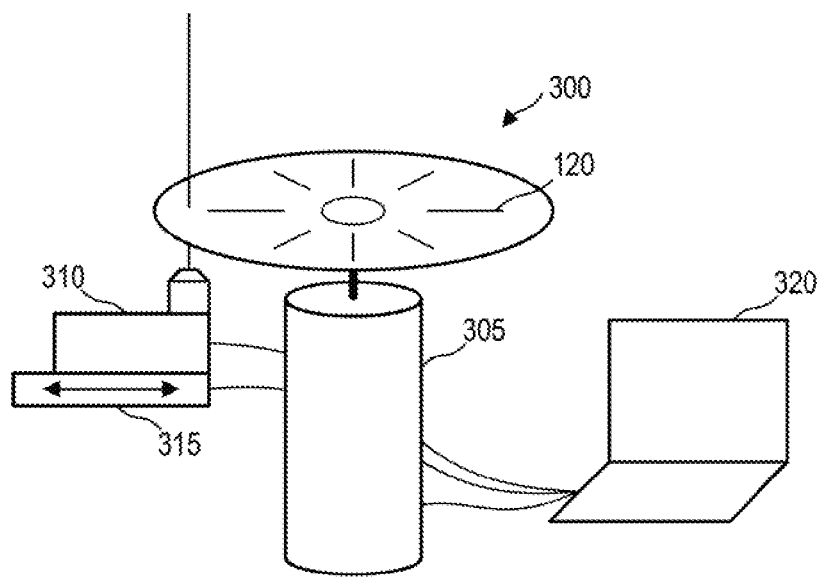
FIG. 3 is a schematic illustration of a system according to an embodiment of the present invention.

FIG. 3 is a schematic illustration of a system according to an embodiment of the present invention. The system 300 may include the disk 100 of FIG. 1 with one or more cell quantification areas 120. A motor 305 may be coupled to the disk 100 and configured to spin the disk 100, generating centrifugal forces. A detection module 310 may be positioned to detect signal from label moieties in a detection region of the cell quantification area 120, as will be described further below. An actuator 315 may be coupled to the detection module 310 and configured to move the detection module along the detection region in some examples. A processing device 320 may be coupled to the motor 305, the detection module 310, and/or the actuator 315 and may provide control signals to those components. The processing device 320 may further receive electronic signals from the detection module 310 corresponding to the label moiety signals received by the detection module 310. All or selected components shown in FIG. 3 may be housed in a common housing in some examples. Microfluidic disks may be placed on the motor 305 and removed, such that multiple disks may be analyzed by the system 300.

The motor 305 may be implemented using a centrifugation and/or stepper motor. The motor 305 may be positioned relative to the detection module 310 such that, when the disk 100 is situated on the motor 305, the disk is positioned such that a detection region of the cell quantification area 120 is exposed to the detection module 310.

The detection module 310 may include a detector suitable for detecting signal from label moieties affixed to cells to be quantified. The detector may include, for example, a laser and optics suitable for optical detection of fluorescence from fluorescent labels. In other examples, other detectors, such as electronic detectors, may be used. The actuator 315 may move the detector in some examples where signal may be detected from a variety of locations of the microfluidic disk 100, as will be described further below.

In other examples, although not explicitly shown in FIG. 3, one or more actuators may be coupled to the motor 305 and/or disk such that the disk is moved relative to the detection module responsive to signals from the processing device, as will be described further below.

The processing device 320 may include one or more processing units, such as one or more processors. In some examples, the processing device 320 may include a controller, logic circuitry, and/or software for performing functionalities described herein. The processing device 320 may be coupled to one or more memories, input devices, and/or output devices including, but not limited to, disk drives, keyboards, mice, and displays. The processing device may provide control signals to the motor 305 to rotate the disk 100 at selected speeds for selected times, as will be described further below. The processing device may provide control signals to the detection module 310, including one or more detectors and/or actuators, to detect signals from the label moieties and/or move the detector to particular locations, as will be described further below. The processing device may develop these control signals in accordance with input from an operator and/or in accordance with software. The software may include instructions encoded one or more memories configured to cause the processing device to output a predetermined sequence of control signals. The processing device 320 may receive electronic signals from the detection module 310 indicative of the detected signal from label moieties. The processing device 320 may quantify cells in a fluid sample based on the signals received from the detection module 310, as will be described further below. Accordingly, the processing device 320 may perform calculations as will be described further below. The calculations may be performed in accordance with software including one or more executable instructions stored on a memory causing the processing device to perform the calculations. Results may be stored in memory, communicated over a network, and/or displayed. It is to be understood that the configuration of the processing device 320 and related components is quite flexible, and any of a variety of computing systems may be used including server systems, desktops, laptops, controllers, and the like.

Having described examples of microfluidic disks and systems in accordance with embodiments of the present invention, methods for quantifying a number of particles in a fluid sample will now be described. Some discussion will also be provided regarding mechanisms for sedimentation and centrifugation. The discussion regarding mechanisms is provided as an aid to understanding examples of the present invention, but is in no way intended to limit embodiments of the present invention. That is, embodiments of the present invention may not employ the described mechanisms.

Sedimentation of spheres may occur within a viscous fluid under the influence of a gravitational field (which may be natural or induced by centrifugation). The settling velocity of approximately spherical particles, such as cells, may be described by Stoke's flow equations:

$$V_s = \frac{2}{9}\frac{(\rho_p - \rho_f)}{\mu}gR^2;$$

where $V_s$ is the sedimentation velocity, $\mu$ is the fluid viscosity, $\rho_p$ is the density of the particle, $\rho_f$ is the density of the fluid, g is acceleration due to effective gravity, and R is the particle radius. Note that sedimentation rate scales with the square of particle radius and therefore a small difference in cell radius may form a basis for separation of cells in some examples, as the cells may sediment at a different rate. There is also a linear dependence of sedimentation rate with the difference in density between the particle and the surrounding fluid, which may also be an effective mechanism for separation. Accordingly, cells or other particles may be separated according to their density and/or radius, as the cells will have different sedimentation velocities. Separation of cells using these principles may be referred to as "rate zonal centrifugation."

Table 1, above, provided example densities of components of whole blood and various components. Table 2, below, includes example diameter, in microns, of those components.

TABLE 1

Example diameters of blood components

| Component | Diameter (microns) |
|---|---|
| Whole Blood | N/A |
| Plasma | N/A |
| Red blood cells | 2.5-7 |
| Granulocytes | 8 |
| Monocytes | 8.5 |
| Lymphocytes | 6.5 |

Figure 4:
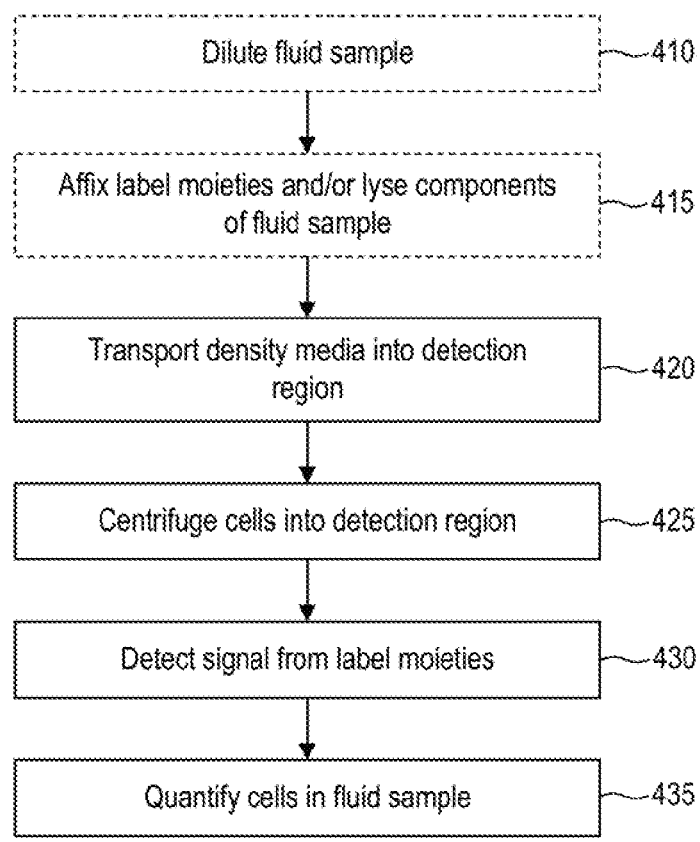
FIG. 4 is a flowchart illustrating a method according to an embodiment of the present invention.

FIG. 4 is a flowchart illustrating a method according to an embodiment of the present invention. In block 410 a fluid sample including a quantity of particles may be diluted. Block 410 may be followed by block 415 in which sample preparation of the fluid sample may occur. For example, in block 415 label moieties may be affixed to the quantity of particles. Alternatively or in addition, in block 415, components of the fluid sample may be lysed. Block 415 may be followed by block 420. In block 420, density media may be transported into a detection region of a microfluidic disk. Block 420 may be followed by block 425. In block 425, the quantity of particles in the fluid sample may be transported toward the detection region using centrifugal force. The quantity of particles may be transported through the density media. Block 425 may be followed by block 430. In block 430, signal may be detected from the label moieties affixed to the quantity of cells. Block 430 may be followed by block 435. In block 435, the quantity of cells may be quantified using the signal detected from the label moieties.

Figure 5:
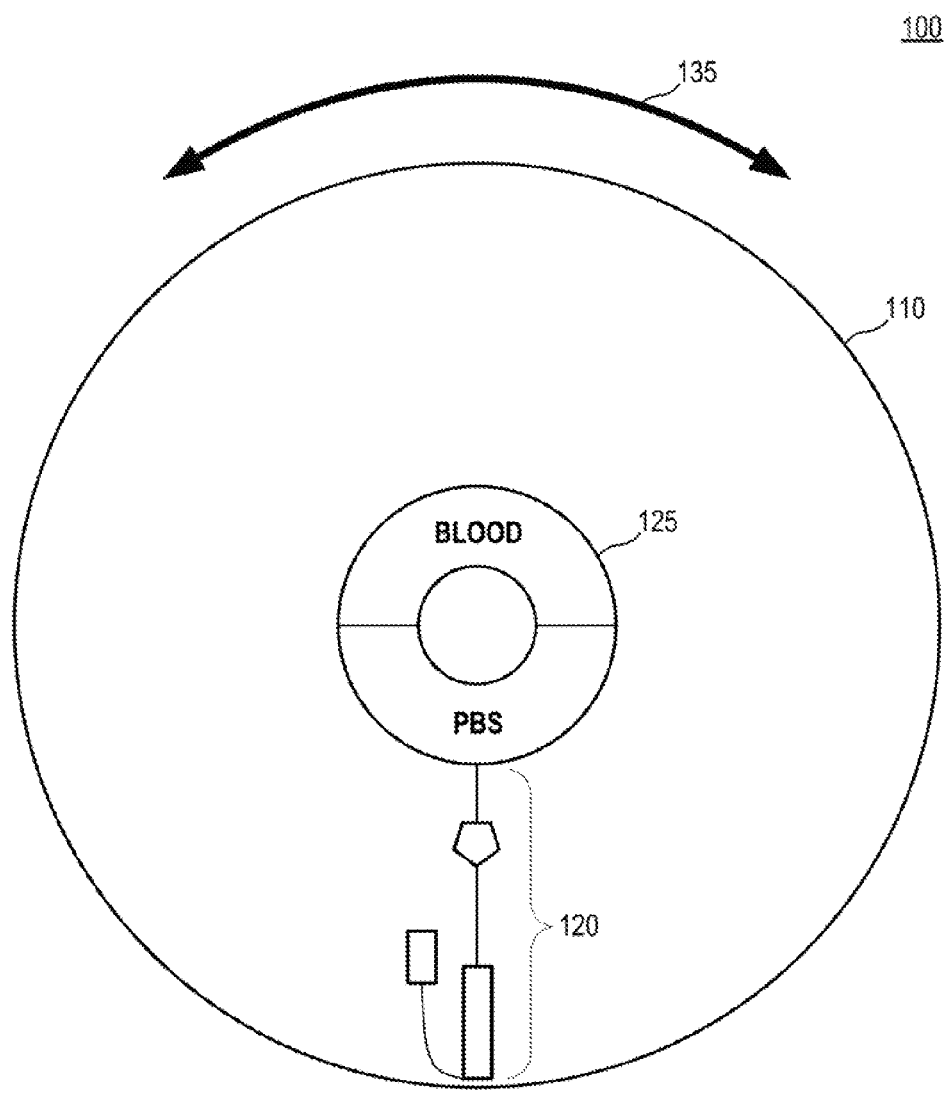
FIG. 5 is a schematic illustration of a microfluidic disk including blood and PBS in the fluid inlet port.

In block 410 a fluid sample may be diluted. The fluid sample may be introduced to a microfluidic disk, such as the disk 100 of FIGS. 1 and 2 before or after dilution. Any of a variety of suitable fluid samples may be used including, but not limited to, whole blood, buffer solutions, saliva, urine, cerebrospinal fluid, mixed cell culture, tissue homogenates, or other biological fluid samples. Generally, the fluid sample will include a quantity of particles, such as cells, to be measured in accordance with embodiments of the present invention. As has been described above, in one example, whole blood may be diluted to a density less than that of a density media used. In one example, a density media having a density of 1.06 is used while the whole blood may be diluted to a density of 1.03 using a 1:1 dilution with a salt solution such as PBS. FIG. 5 is a schematic illustration of the microfluidic disk 100 including blood and PBS in the fluid inlet port 125. The microfluidic disk may be spun, for example using the motor 305 of FIG. 3, such that the blood and PBS solution are mixed in block 410 of FIG. 4. In other examples, a fluid sample may be diluted or otherwise mixed prior to introduction to the microfluidic disk 100.

In block 415, any of a variety of sample preparation operations may occur. For example, label moieties may be affixed to cells in the fluid sample and/or components of the fluid sample may be lysed. Referring back to FIG. 2, in some examples, label moieties and/or lysing agent(s) may be contained in the chamber 220. The microfluidic disk 100 may be spun, for example using the motor 305 of FIG. 3, such that the fluid sample including a quantity of cells are transported into and/or through the chamber 220. The fluid sample including the quantity of cells may be transported continuously through the chamber 220 while lysis and/or labeling occur, or in some examples, the spinning of the microfluidic disk 100 may be stopped for a time to allow for labeling and/or lysis. Suitable lysis agents and label moieties have been described above. In some embodiments, particles may be bound to target analytes in the fluid sample, such as cells, for quantification of the target analyte. For example, particles made from silica, gold, iron oxide, or combinations thereof may be coated with an antibody for recognition of proteins on the surface of certain cells. Other particles may be used. The particles may be included in the mixing chamber 220 in some examples. The particles may bind to the certain cells and increase the sedimentation rate of certain cells on binding, allowing the certain cell types to be selectively removed from the sample during centrifugation for quantification and/or post-processing. Particles coated with molecules other than antibodies, such as integrins or selectins, may also be used for specific cell binding. In one example, silica beads coated with an antibody against the protein CD14 may be used to specifically bind to monocytes and cause the bound monocytes to sediment more quickly than other cell types.

In other examples, labeled antibodies that may recognize proteins on the surface of specific cells may be included in the chamber 220 in addition or instead of DNA labeling and/or lysis agents. Cells labeled in this manner may be separated by size and density, as described below, and the labeled cells may have additional labeling chara.

Referring back to FIG. 4, in block 420, the density media may be transported into the detection region, such as the detection region 230 of FIG. 2. In some examples, density media may already be present in the detection region 230 and need not be transported in a separate operation. In some examples, the density media may be stored in the chamber 235. The microchannel 240 may have a width selected to serve as a valve, such that a spin rate over a threshold amount is required to initiate a flow of the density media 235 out of the chamber 235 through the microchannel 240. In some examples, the microchannel 240 has a width and spin rates for one or more of blocks 410-415 are selected such that the density media is retained in the chamber 235 while the fluid sample is transported toward the detection region 230 through the chamber 220. A spin rate of the microfluidic disk 100 may be increased at the block 420 to initiate or enhance a flow of the density media 235 into the detection region 230. In this manner, the microchannel 240 may function as a valve. Other valve structures may be used in other examples. In block 420, the valve may be activated to allow the flow of density media into the detection region 230.

In block 425, cells in the fluid sample may be centrifuged into the detection region. Centrifugal force may be used to continue to transport the fluid sample toward the detection region 230 of FIG. 2. The microfluidic disk 100 may be spun, using for example the motor 305 of FIG. 3, to transport the fluid sample containing a quantity of labeled cells into the detection region 230.

Figure 6:
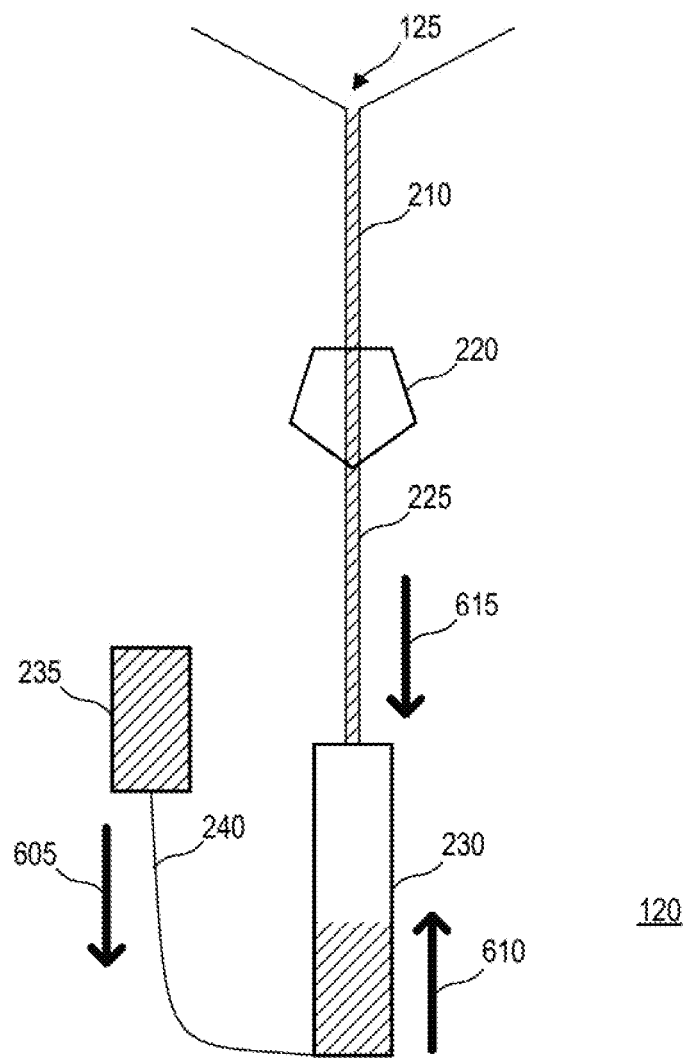
FIG. 6 is a schematic illustration of a cell quantification area showing directions of fluid flow in accordance with an embodiment of the present invention.

FIG. 6 is a schematic illustration of the cell quantification area 120 showing directions of fluid flow in accordance with an embodiment of the present invention. The microfluidic disk 100 may be spun at a rate sufficient to cause the density media to be transported from the chamber 235 to the detection area 230 through the microfluidic channel 240 using centrifugal force. The density media accordingly may flow in the direction shown by arrows 605 and 610. A fluid sample may be transported by the same centrifugal forces from the inlet 125 toward the detection region 230, as shown by the arrow 615.

As has been described above, the density media may have a density greater than that of the fluid sample, but lower than that of the cells to be quantified. Accordingly, as the flow of fluid sample indicated by the arrow 615 meets the flow of density media 610, the cells from the fluid sample may be transported through the density media using centrifugal force, while remaining components of the fluid sample may not be transported through the density media. For example, hemoglobin spilled from red cell lysis may remain suspended and not transported through the density media due to in part to the smaller particle size compared to cells. Red blood cell membranes may remain suspended and not transported through the density media due to their lower density than the density media. Further, excess label moieties may not be transported through the density media. Labeled white blood cells, however, may be transported through the density media.

Referring back to FIG. 4, in block 430, a signal may be detected from label moieties affixed to the cells. The signal may be detected in any of a variety of ways, and the detection methodology may be selected for compatibility with the label moiety and quantification technique described further below. In the case of a fluorescent label moiety, an optical detector may be used to detect fluorescence emitted by the label moieties. The rate at which labeled cells are transported through the density media may depend on the density and radius of the labeled cells, as was described above using theoretical principles. Accordingly, cells may be separated from the fluid sample based on their density and/or radius.

Figure 7:
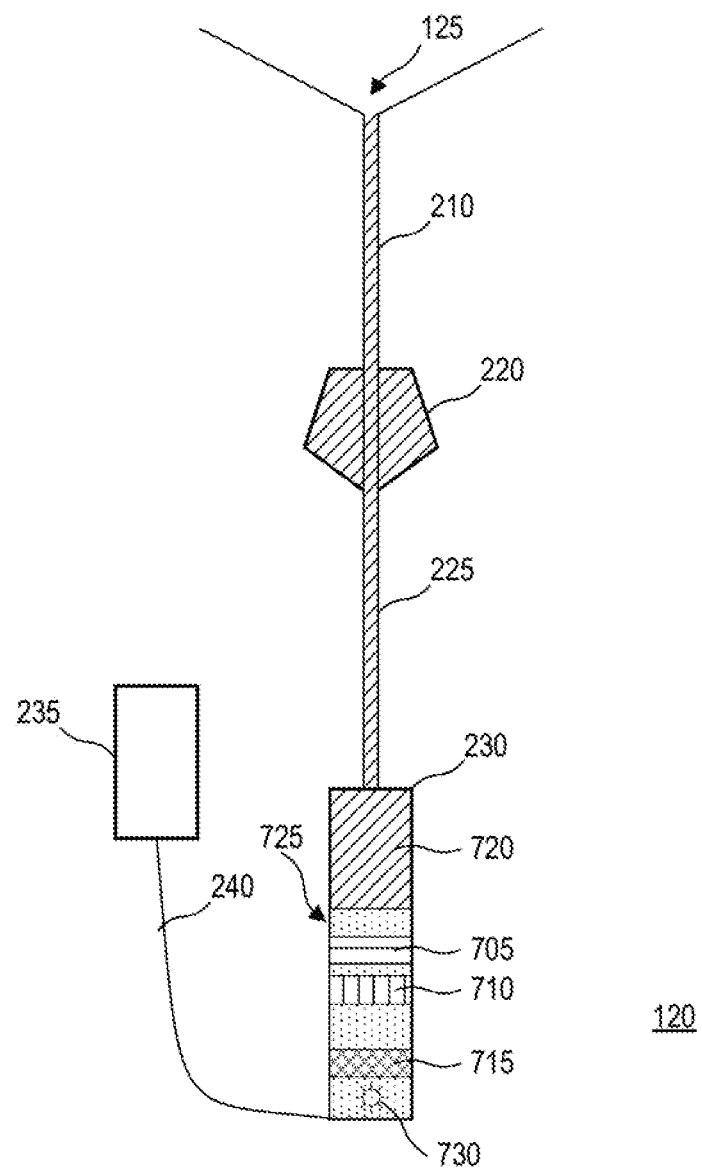
FIG. 7 is a schematic illustration of a cell quantification area showing separated cells in accordance with an embodiment of the present invention.

FIG. 7 is a schematic illustration of the cell quantification area 120 showing separated cells in accordance with an embodiment of the present invention. As the microfluidic disk 100 spins and applies a centrifugal force to the fluid sample, cells may be separated by their radius and/or density into bands. Bands 705, 710, and 715 are shown in FIG. 7 within the detection region 230. The band 705 may correspond to lymphocytes, the band 710 to monocytes, and the band 715 to granulocytes. Components of the fluid sample 720 which are less dense than the density media remain separated from the density media 725 in the detection region. In some embodiments, an optical detector, such as the detection module 310 of FIG. 3, may be positioned to detect signal from label moieties at a location 730. As the separated labeled cell bands 705, 710, and 715 are transported through the density media toward the detection location 730, they may be optically detected.

Table 3 below provides an average time to the detection location 730 for different cell types based on the 1.06 density media described above, whole blood diluted to a 1.03 density, and a detector positioned 4 mm from an interface between the whole blood fluid sample and the density media. A 12 cm diameter microfluidic disk is assumed, with a detection region 1 cm away from the edge of the disk.

TABLE 3

Example migration time of blood components inviscous media
Media density = 1.06
Viscosity = 15 centipoise
Spin rate = 5400 RPM

| Cell Type | Migration Time (s) |
|---|---|
| Red blood cells | 66 |
| Granulocytes | 70 |
| Monocytes | 175 |
| Lymphocytes | 226 |

Note that, in some examples, red blood cells may not be present in the sample, and/or may have been lysed.

Figure 8:
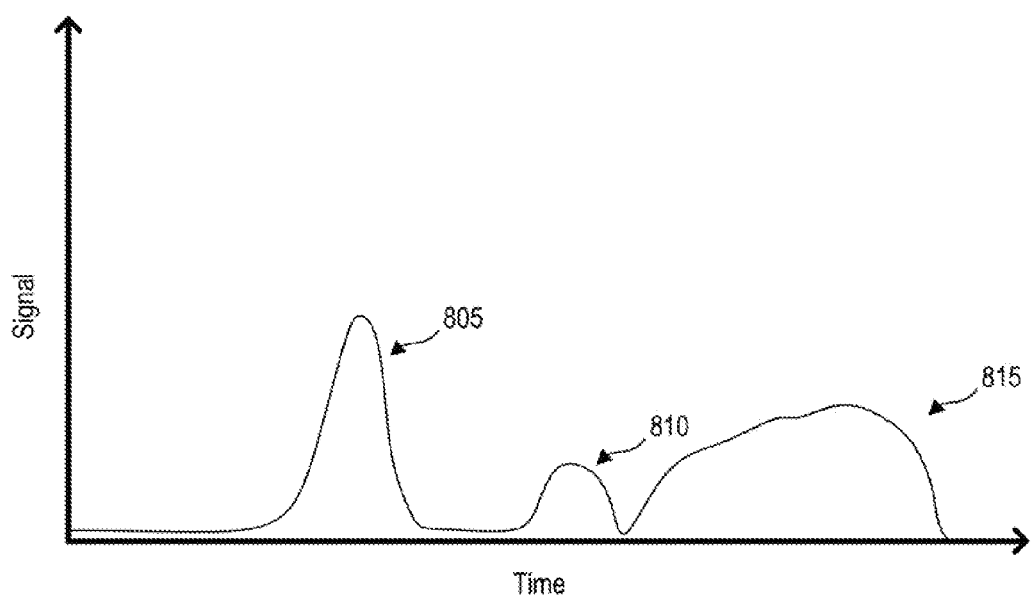
FIG. 8 is a schematic illustration of signal detected over time from labeled cells in accordance with an embodiment of the present invention.

FIG. 8 is a schematic illustration of signal detected over time from labeled cells in accordance with an embodiment of the present invention. Referring back to FIG. 7, the granulocyte band 715 may be the first to pass the detection location 730, generating a detected signal peak 805 in FIG. 8. The granulocyte band 715 is the first to reach the detection location at least because the granulocytes may be more dense than the monocytes and lymphocytes. The monocyte band 710 may be the next to reach the detection location, generating a detected signal peak 810. The monocyte band 710 may reach the detection location after the granulocyte band 715 because the monocytes may be less dense than the granulocytes, as described above, and may have a larger diameter than the lymphocytes. The lymphocyte band 705 may then be the last to pass the detection location 730, generating a detected signal peak 815. In some examples, the peaks may overlap, for example, if the detection region is not long enough to allow for distinct separation of the peaks.

Referring again to FIG. 4, in block 435, the detected cells may be quantified. The quantification may be based on the signal detected from the label moieties in block 430, and any of a variety of quantification techniques may be used. The quantification may be performed, for example, by the processing device 320 of FIG. 3 based on signals received from the detection module 310. Referring to FIG. 8, a total number of white blood cells may be quantified by integrating the signal received over time. A relative number of granulocytes, monocytes, and/or lymphocytes may be calculated by integrating the respective signal peaks over time.

Following a sufficient amount of centrifugation, the labeled cells may accumulate in a pellet at the peripheral portion of the detection region 230 of FIG. 2. That is, all labeled white blood cell components may eventually be driven to an outermost portion of the detection region 230 by centrifugal force. An absolute total cell count may be obtained by measuring the height of the pellet. The cells may occupy a volume consistent with random close packing of spheres, where the pellet may include 64 percent cells and 36 percent fluid-filled space. In examples where the cells may not approximate spheres, other percentages may be used. In this manner, a height of the pellet may be proportional to the total number of labeled cells. The pellet height may be measured, for example, by the detection module 310 of FIG. 3, or by examination with a microscope or other signal detection apparatus. The total cell concentration may be calculated from the pellet height and detection region geometry as follows:

$$CellConcentration = \frac{0.64 * Thickness * Width}{CellVolume * SampleSize} * PelletHeight,$$

where the Thickness and Width are dimensions of the detection region in which the pellet has formed. In one example, 2 μL of whole blood may be analyzed in a detection region which is 0.5 mm wide and 80 μm thick. An average white blood cell diameter may be 7.5 μm, and the sedimented pellet height of the white cell layer may be 86 μm. Accordingly, a white blood cell concentration of $5 \times 10^6$/mL may be calculated.

In some examples, a red blood cell count may also be measured, along with a white blood cell count, in accordance with embodiments of the present invention. For example, referring back to FIG. 1, an additional cell quantification area may be provided in addition to or instead of the cell quantification area 120. The additional cell quantification area may not include a chamber for cell lysis, and accordingly, red blood cells may also be transported through the density media described above. The red cell pellet height following sedimentation may be used as described above to calculate a number or concentration of red blood cells. In this manner, both red and white blood cell counts may be obtained from a same microfluidic disk in some examples.

In some examples, a centrifugal force may be reduced or removed after one or more white blood cell components have been separated from the fluid sample as illustrated in FIG. 7. Instead of transporting the bands 705, 710, 715 past a detection location 730, a detector may be scanned along the detection region 230 to detect the bands 705, 710, 715. For example, referring to FIG. 3, the actuator 315 may move the detection module 310 along a length of the detection region on the microfluidic disk 100. Signal may be detected from label moieties at different distances in the detection region, similar to the signal shown in FIG. 8, except with the x axis representative of distance. In this manner, signal may be detected from the separated components, and an integral of the signal peaks may yield relative cell counts, as generally described above.

Accordingly, embodiments of devices, systems, and methods for measuring cells in a fluid sample have been described above. Embodiments described include transporting a quantity of cells through a density media having a density that is greater than the fluid sample but less than a density of the cells. Further embodiments may have different device, system, and method configurations to measure cells in a fluid sample using centrifugal forces and density media.

Figure 9:
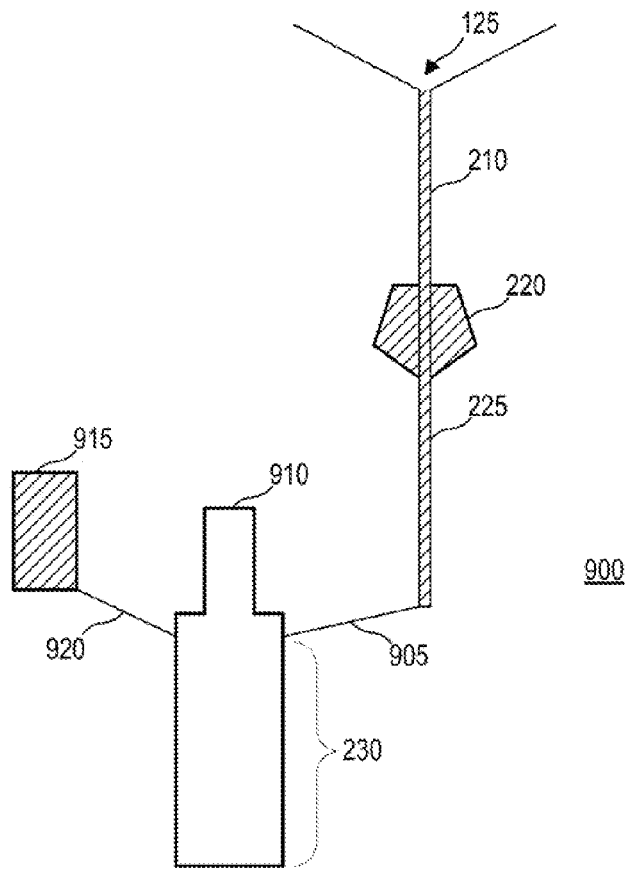
FIG. 9 is a schematic illustration of another embodiment of a cell quantification area arranged in accordance with the present invention.

FIG. 9 is a schematic illustration of another embodiment of a cell quantification area 900 arranged in accordance with the present invention. The channel 225 may be coupled to the detection region 230 by a microfluidic channel 905, which may have a dimension selected such that the microfluidic channel 905 may serve as a valve, allowing fluid flow into the detection area responsive to a threshold level of centrifugal force. A chamber 915 may be coupled to the detection area 230 and configured to contain a density media. Another chamber 910 may be coupled to the detection area 230 and configured to contain another density media. The density media in the chamber 915 may be less dense than the density media in the chamber 910. So for example, the density media in the chamber 910 may have a density greater than a density of a fluid sample but less than a density of one cell type in the fluid sample. The density media in the chamber 915 may have a density greater than a density of a fluid sample, but less than the density media in the chamber 910 and less than a density of another cell type in the fluid sample. As will be described further below, the density media may be placed adjacent one another in the detection area 230, and cells in a fluid sample may be drawn through the density media to the interface between the density media.

Figure 10:
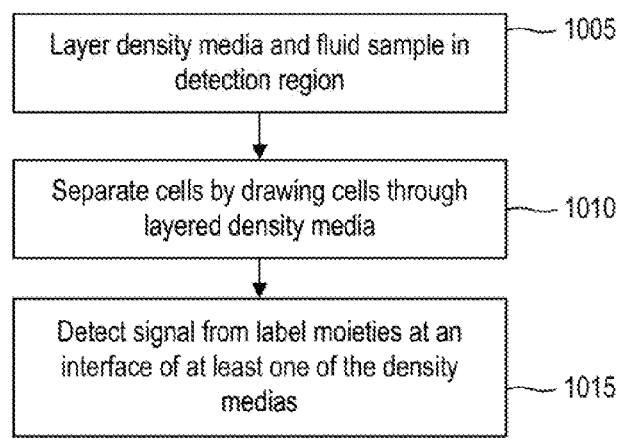
FIG. 10 is a flowchart illustrating an example method for measuring cells according to an embodiment of the present invention.

FIG. 10 is a flowchart illustrating an example method for measuring cells according to an embodiment of the present invention. Prior to block 1005, one or more of the sample preparation steps, such as those described above with reference to blocks 410 and 415 of FIG. 4, may be performed. In block 1005, density media and a fluid sample may be layered in a detection region. Block 1005 may be followed by block 1010 in which cells may be separated from the fluid sample by drawing the cells through the layered density media. Block 1010 may be followed by block 1015. In block 1015, signal may be detected from label moieties affixed to cells at an interface of at least one of the density media in the detection region.

In block 1005, density media and a fluid sample may be layered in a detection region. As has been described above, multiple density media may be used, including two density medias having different densities. The density media and fluid sample may be layered in a single step, or the density medias may be layered first, followed by the fluid sample. Layering may be achieved by transporting individual ones of the density media and fluid sample sequentially into the detection region. In other examples, layering may be achieved by spinning a microfluidic disk such that the density media and fluid sample are transported into the detection region.

Figure 11:
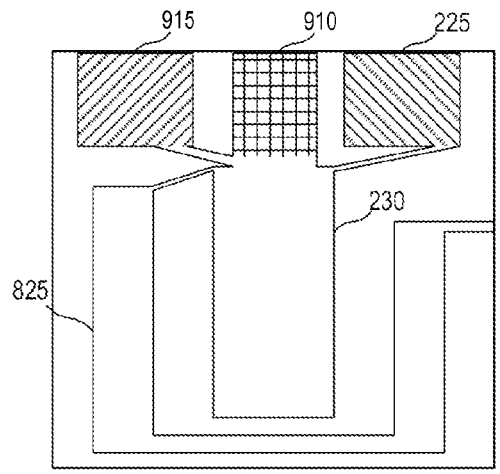
FIG. 11 is a schematic illustration of a portion of a cell quantification region in accordance with an embodiment of the present invention.

FIG. 11 is a schematic illustration of a portion of the cell quantification region 900 of FIG. 9 showing a density media loaded into the chamber 910, another density media loaded into the chamber 915, and a fluid sample loaded in the channel 225. The microfluidic disk may then be spun to generate a centrifugal force to cause the density medias and the fluid sample to enter the detection region 230. The density media in the chamber 910 may be denser than the density media in the chamber 915, which may in turn be denser than the fluid sample in the chamber 225. In one example, the density media in the chamber 910 may have a density 1.091, which may be implemented using a 70% Percoll concentration, while the density media in the chamber 915 may have a density of 1.078, which may be implemented using a 60% Percoll concentration. Other densities and concentrations may also be used.

Figure 12:
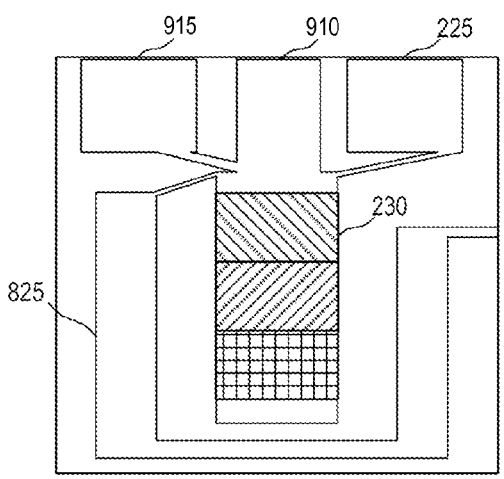
FIG. 12 is a schematic illustration of a portion of a cell quantification area following layering of density media.

FIG. 12 is a schematic illustration of the portion of the cell quantification area 900 of FIG. 11 following layering. The density media from the chamber 910 has been transported to a peripheral region of the detection region 230, followed by the density media from the chamber 915, and the fluid sample from the channel 225. In one embodiment, the layering process included spinning a microfluidic disk at 100 RPM for thirty seconds. The time and speed selected will vary based on the channel and chamber dimensions and fluids involved.

In block 1010, cells may be separated from the fluid sample by drawing the cells through the layered density media using a centrifugal force. As has been described above, block 1010 may be implemented by spinning a microfluidic disk. Components of the fluid sample denser than both density media may be drawn toward the far peripheral portion of the detection region. Components of the fluid sample denser than one density media, but less dense than another may separate to a location at the interface between the density medias. Components of the fluid sample which are less dense than both density media may remain above both density media.

Figure 13:
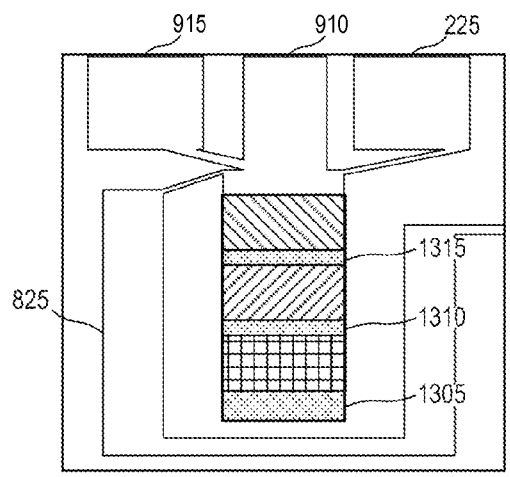
FIG. 13 is a schematic illustration of a portion of a cell quantification region following cell separation of a whole blood sample.

FIG. 13 is a schematic illustration of the portion of cell quantification region 900 of FIG. 12 following cell separation of a whole blood sample. Unlysed red blood cells, if present, may be transported to a peripheral location 1305 of the detection region. Granulocytes may be separated at a band 1310 located at an interface between the two density medias. The granulocytes may be less dense than the density media from the chamber 910, but more dense than the density media from the chamber 915. Monocytes and lymphocytes may be separated together at a band 1315, and may not be separated from one another, as both may be less dense than the density media from the chamber 915.

As generally described above, a detection module may be positioned to detect one or more of the bands 1305, 1310, and 1315. The detection module may include an actuator, as shown in FIG. 3, to move a detector along the detection region and detect signal from each of the bands. The signal peaks detected at particular distances may be integrated to quantify a relative count of cells pertaining to each density range. In some cell count application which utilize relative granulocyte count, such as radiation biodosymetry or sepsis, this embodiment may be advantageous since the granulocytes are separated from remaining components.

Figure 14:
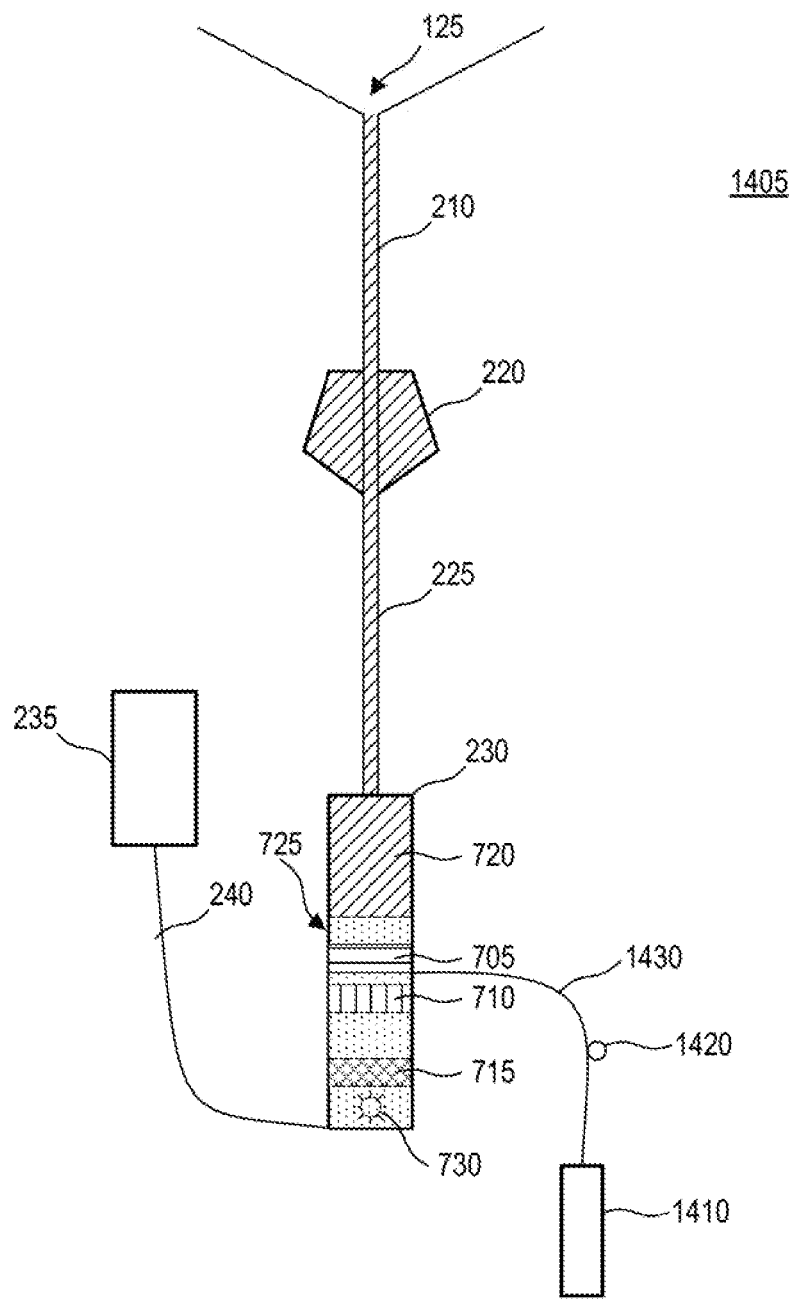
FIG. 14 is a schematic illustration of a portion of a cell quantification area including a post-processing area in accordance with an embodiment of the present invention.

Examples of the separation and quantification of particles in a sample fluid have accordingly been described above. In some examples, a separated component of a sample fluid may be subject to one or more post-processing procedures. FIG. 14 is a schematic illustration of a portion of a cell quantification area 1405 including a post-processing area 1410. The cell quantification area 1405 is shown including components shown and described above with reference to FIG. 7, and like reference numbers are retained. The detection region, however, may be coupled to a post-processing area 1410 by a channel 1430. Access between the detection region and the post-processing area 1410 may be controlled by a valve 1420. By selecting a time at which the valve 1420 is opened, the components diverted to the post-processing area 1410 may be selected. That is, as components sediment out of a fluid sample and travel toward an end of the detection region, they may be diverted toward the post-processing area 1410 once the valve 1420 is opened. Accordingly, particles may be diverted to the post-processing area 1410 prior to complete sedimentation of all particles.

The post-processing area 1410 may be a channel, chamber, and/or reservoir of substantially any shape or size and may be partially defined by a same substrate as the detection region. Any of a variety of post-processing procedures or treatments may occur in the post-processing area 1410 included, but not limited to lysis, PCR, immunoassay, and/or biochemical analysis. In other examples, no post-processing procedures may occur, but a particular component of the sample may be stored in the post-processing area 1410.

In some examples, bacteria and/or viruses may be separated from a fluid sample. Bacteria and/or viruses are generally smaller than mammalian cells, and may accordingly sediment much more slowly or not at all through a density media during centrifugation. In some examples, bacteria and/or viruses may be labeled and quantified in an analogous manner to that described above for particles to quantify infection load in a fluid sample. The smaller particles such as the bacteria and/or viruses may generally be detected at or near a top of the density media. Referring to FIG. 14, the bacteria and/or viruses may be diverted to the post-processing area 1410 by opening the valve 1420. Centrifugation may divert the bacteria and/or viruses to the post-processing area 1410. Further processing such as lysis, PCR, immunoassay, or harvesting of the contents of the post-processing area 1410 for subsequent culture may be performed to identify bacteria and/or viruses.

As another example, the valve 1420 of FIG. 14 may be opened during centrifugation at a time when lymphocytes are expected to be above the intersection of the channel 1430 and the detection region 230. The lymphocytes may then be diverted to the post-processing area 1410. Additional analysis of the separated lymphocytes may then be performed, such as PCR for gene expression analysis.

As another example, tumor cells, which may be denser than other components of a fluid sample, may be separated, counted, and analyzed from a biopsy homogenate by removing the smaller cells through the channel 1430. More generally, a particular cell population may be selected from a mixture of components in a fluid sample for further biochemical analysis based on the differential size and density of the cell population. The cell population diverted to the post-processing area 1410 may also be counted or quantified in the post-processing area 1410 using methods described above.

From the foregoing it will be appreciated that, although specific embodiments of the invention have been described herein for purposes of illustration, various modifications may be made without deviating from the spirit and scope of the invention.

What is claimed is:

1. A method comprising:
    introducing a fluid sample containing a quantity of white blood cells into a channel defined in part by a substrate;
    forming complexes which include label moieties affixed to at least a portion of the quantity of white blood cells;
    providing first and second density media in separate chambers defined at least in part by the substrate wherein the first density media has a density different from that of the second density media and wherein the first and second density media have a density lower than a density of the white blood cells and higher than a density of the fluid sample;
    spinning the substrate to transport the first and second density media from the separate chambers into a detection region defined in part by the substrate;
    transporting the quantity of white blood cells toward the detection region comprising the layered density media;
    spinning the substrate such that at least a portion of the quantity of white blood cells is transported through at least a portion of the first or second density media; and
    detecting signals from the label moieties affixed to the at least a portion of the quantity of white blood cells, including detecting signals from label moieties near an interface of the first and second density media.

2. The method of claim 1, wherein said spinning the substrate such that at least a portion of the quantity of white blood cells is transported through the density media comprises spinning the substrate such that at least a portion of the fluid sample is restricted from transport through the first or second density media.

3. The method of claim 1, further comprising:
    transporting the quantity of white blood cells through a labeling region defined in part by the substrate, wherein the labeling region contains a quantity of the label moieties.

4. The method of claim 1, wherein said spinning the substrate to layer a first and second density media in a detection region defined in part by the substrate comprises spinning the substrate such that the first and second density media are transported from the separate chambers toward the detection region.

5. The method of claim 1, wherein the fluid sample comprises whole blood.

6. The method of claim 1, wherein said detecting signals from the label moieties affixed to the at least a portion of the quantity of white blood cells comprises transporting the at least a portion of the quantity of white blood cells passed a detector, in part using centrifugal force.

7. The method of claim 1, wherein a density of at least some of the white blood cells is determined based, at least in part, on other particles of a particular density bound to the at least some of the white blood cells.

8. The method of claim 1, wherein said detecting signals from the label moieties affixed to the at least a portion of the quantity of white blood cells comprises moving a detector along at least a portion of the detection region.

9. The method of claim 1, wherein said label moieties comprise DNA dye molecules.

10. The method of claim 1, wherein said label moieties comprise lipid dye molecules.

11. The method of claim 1, wherein said label moieties comprise antibodies with affinity for specific cell surface proteins.

12. The method of claim 1, wherein a portion of the white blood cells is diverted to a separate chamber in fluid communication with the channel prior to complete sedimentation of the white blood cells, wherein the method comprises diverting the portion of the white blood cells, at least in part, by opening a valve at a selected time during sedimentation of the white blood cells when the portion of the white blood cells is expected to be at a particular location in the channel.

13. The method of claim 1, further comprising calculating a number of the at least a portion of the quantity of white blood cells based, at least in part, on the signals received from the label moieties.

14. The method of claim 13, wherein said spinning the substrate such that at least a portion of the quantity of white blood cell is transported through the density media comprises forming a pellet of cells at an end of the detection region, and wherein said calculating a number of the at least a portion of the quantity of white blood cells based, at least in part, on the signals received from the label moieties is based, at least in part, on dimensions of said pellet.

15. The method of claim 1, wherein the quantity of white blood cells includes one or more of a quantity of lymphocytes, monocytes, and granulocytes, and wherein the first density media have a first density lower than a density of the granulocytes but higher than a density of the lymphocytes or monocytes, and wherein the second density media have a second density lower than a density of the lymphocytes or monocytes but higher than the density of the fluid sample.

16. The method of claim 1, wherein the quantity of white blood cells includes a quantity of lymphocytes, a quantity of monocytes, and a quantity of granulocytes, the method further comprising forming, along a length of the detection region, a first band including at least a portion of the quantity of lymphocytes, a second band including at least a portion of the quantity of monocytes, and a third band including at least a portion of the quantity of granulocytes.

17. The method of claim 1, wherein the quantity of white blood cells includes a quantity of lymphocytes, a quantity of monocytes, and a quantity of granulocytes, the method further comprising forming, along a length of the detection region, a first band including at least a portion of the quantity of lymphocytes and at least a portion of the quantity of monocytes and a second band including at least a portion of the quantity of granulocytes.

18. The method of claim 1, wherein the substrate comprises a reservoir in fluid communication with the channel and wherein the reservoir is configured to hold lysis agents and/or label moieties.

19. The method of claim 18, wherein the method further comprises lysing components of the fluid sample.

\* \* \* \* \*